United States Patent [19]

Sircar et al.

[11] Patent Number: 4,581,458

[45] Date of Patent: Apr. 8, 1986

[54] 5-SUBSTITUTED-3-AMINOISOXAZOLE COMPOUNDS

[75] Inventors: Jagadish C. Sircar, Ann Arbor; Thomas Capiris, Plymouth, both of Mich.

[73] Assignee: Warner-Lambert Company, Morris Plains, N.J.

[21] Appl. No.: 660,356

[22] Filed: Oct. 12, 1984

Related U.S. Application Data

[60] Division of Ser. No. 575,411, Feb. 2, 1984, Pat. No. 4,489,077, which is a continuation-in-part of Ser. No. 478,016, Mar. 23, 1983, abandoned.

[51] Int. Cl.⁴ ........................................... C07D 261/14
[52] U.S. Cl. ..................................................... 548/246
[58] Field of Search ................................ 548/246, 247

[56] References Cited

U.S. PATENT DOCUMENTS 4,268,679  5/1981  Lavanish ............................. 548/247
4,354,030  10/1982  Barow et al. ....................... 548/247

FOREIGN PATENT DOCUMENTS 40-11616 of 1965 Japan ................................... 548/246

OTHER PUBLICATIONS

Barton and Ollis, *Comprehensive Organic Chemistry*, Pergamon, New York (1979), p. 915.
Greene, *Protective Groups in Organic Synthesis*, John Wiley, New York (1981), pp. 224–227.

Primary Examiner—Donald G. Daus
Assistant Examiner—A. Hendricks
Attorney, Agent, or Firm—Jerry F. Janssen

[57] ABSTRACT

4-Hydroxy-N-[5-[(substituted hetero)methyl]-3-isoxazolyl]-2H-1,2-benzothiazine-3-carboxamide 1,1-dioxides as agents for treating pain in mammals resulting from inflammation.

6 Claims, No Drawings

5-SUBSTITUTED-3-AMINOISOXAZOLE COMPOUNDS

CROSS-REFERENCE TO RELATED APPLICATIONS

This application is a divisional of application Ser. No. 575,411, filed Feb. 2, 1984, now U.S. Pat. No. 4,489,077, which, in turn is a continuation-in-part of application Ser. No. 478,016, filed Mar. 23, 1983, now abandoned.

BACKGROUND OF THE INVENTION

U.S. Pat. Nos. 3,822,258 and 3,787,324 disclose, inter alia certain 4-hydroxy-3-(3-isoxazolylcarbamoyl)-2H-1,2-benzothiazine 1,1-dioxides which are useful as antiinflammatory agents, antipyretics and analgesics. 4-Hydroxy-N-[5-hydroxymethyl)-3-isoxazolyl]-2-methyl, 2H-1,2-benzothiazine-3-carboxamide,1,1-dioxide, the human metabolite of the antiinflammatory drug, isoxicam, has been disclosed in P. E. Borondy, et al, Pharmacologist, 23, 212 (1981) and G. J. Yakatan, Seminars in Arthritis and Rheumatism, 12, (2), suppl. 2, 154 (1982).

DESCRIPTION OF THE INVENTION

The present invention relates to 4-hydroxy-N-[5-[(substituted hetero)methyl]-3-isoxazolyl]-2H-1,2-benzothiazine-3-carboxamide, 1,1-dioxide, i.e., novel analogs of isoxicam where the 5 position of the isoxazole ring contains a substituted heteromethyl group having the following structural formula:

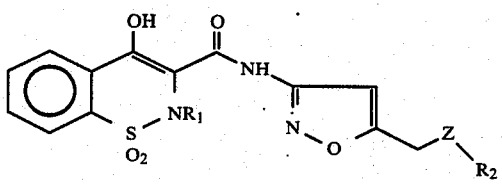

wherein $R_1$ is hydrogen or alkyl of 1 to 6 carbon atoms; Z is 0, $SO_m$ where m is 0, 1, or 2, or $NR_3$ where $R_3$ is hydrogen or alkyl of 1 to 6 carbon atoms; $R_2$ is alkanoyl of 1 to 6 carbon atoms when Z is 0, S or $NR_3$, or $—(CH_2)_nR$ where n is 1 to 10 and R is hydrogen or Ar in which Ar is

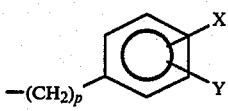

where p is 0 to 10 and X and Y are independently hydrogen, halogen, alkyl of 1 to 6 carbon atoms, trifluoromethyl, alkoxy of 1 to 4 carbon atoms, lower alkylthio of 1 to 4 carbon atoms or hydroxy; or $R_3R_2$ combine with N to form pyrrolidine, piperidine, piperazine, morpholine or thiomorpholine, and pharmaceutically acceptable metal or amine salts thereof.

Preferred compounds of the present invention are those of formula 1 wherein $R_1$ is hydrogen or methyl; Z is 0 or $SO_m$ where m is 0, 1, or 2; $R_2$ is $—(CH_2)_nR$ where n is 1 to 10 and R is hydrogen or Ar in which Ar is

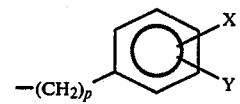

where p is 0 to 10 and X and Y are independently hydrogen, halogen, alkyl of 1 to 6 carbon atoms, trifluoromethyl or alkoxy of 1 to 4 carbon atoms, and pharmaceutically acceptable metal or amine salts thereof.

Also preferred are compounds of the formula 1 wherein $R_1$ is hydrogen or methyl; Z is 0 or $SO_m$ where m is 0, 1, or 2; $R_2$ is $—(CH_2)_nR$ where n is 1 to 10 and R is hydrogen, benzyl, or substituted benzyl, and pharmaceutically acceptable metal or amine salts thereof.

Particularly valuable are:

4-hydroxy-N-[5-(methoxymethyl)-3-isoxazolyl]-2-methyl-2H-1,2-benzothiazine-3-carboxamide 1,1-dioxide;

4-hydroxy-N-[5-[(benzyloxy)methyl]-3-isoxazolyl]-2-methyl-2H-1,2-benzothiazine-3-carboxamide 1,1-dioxide;

4-hydroxy-N-[5-[(butylthio)methyl]-3-isoxazolyl]-2-methyl-2H-1,2-benzothiazine-3-carboxamide 1,1-dioxide;

4-hydroxy-2-methyl-N-[5-[[[5-[(octyloxy)methyl]-3-isoxazolyl]amino]methyl]-3-isoxazolyl]-2H-1,2-benzothiazine-3-carboxamide, 1,1-dioxide;

4-hydroxy-N-[5-[(octyloxy)methyl]-3-isoxazolyl]-2-methyl-2H-1,2-benzothiazine-3carboxamide 1,1-dioxide;

N-[5-[(butylsulfonyl)methyl]-3-isoxazolyl]-4-hydroxy-2-methyl-2H-1,2-benzothiazine-3-carboxamide, 1,1-dioxide;

4-hydroxy-N-[5-(octylthio)methyl]-3-isoxazolyl]-2-methyl-2H-1,2-benzothiazine-3-carboxamide, 1,1-dioxide;

4-hydroxy-2-methyl-N-[5-(octylsulfonyl)methyl]-3-isoxazolyl]-2H-1,2-benzothiazine-3-carboxamide, 1,1-dioxide;

N-[5-[(heptylthio)methyl]-3-isoxazolyl]-4-hydroxy-2-methyl-2H-1,2-benzothiazine-3-carboxamide, 1,1-dioxide;

N-[5-[(heptylsulfonyl)methyl]-3-isoxazolyl]-4-hydroxy-2-methyl-2H-1,2-benzothiazine-3-carboxamide, 1,1-dioxide;

N-[5-[(decylthio)methyl]-3-isoxazolyl]-4-hydroxy-2-methyl-2H-1,2-benzothiazine-3-carboxamide, 1,1-dioxide;

N-[5-[(decylsulfonyl)methyl]-3-isoxazolyl]-4-hydroxy-2-methyl-2H-1,2-benzothiazine-3-carboxamide, 1,1-dioxide;

N-[5-[(heptylsulfinyl)methyl]-3-isoxazolyl]-4-hydroxy-2-methyl-2H-1,2-benzothiazine-3-carboxamide, 1,1-dioxide;

4-hydroxy-2-methyl-N-[5-[(octylsulfinyl)methyl]-3-isoxazolyl]-2H-1,2-benzothiazine-3-carboxamide, 1,1-dioxide;

N-[5-[(decylsulfinyl)methyl]-3-isoxazolyl]-4-hydroxy-2-methyl-2H-1,2-benzothiazine-3-carboxamide, 1,1-dioxide;

4-hydroxy-2-methyl-N-[5-[(nonylthio)methyl]-3-isoxazolyl]-2H-1,2-benzothiazine-3-carboxamide, 1,1-dioxide;

4-hydroxy-2-methyl-N-[5-[(nonylsulfonyl)methyl]-3-isoxazolyl]-2H-1,2-benzothiazine-3-carboxamide, 1,1-dioxide;

N-[5-[(butylsulfinyl)methyl]-3-isoxazolyl]-4-hydroxy-2-methyl-2H-1,2-benzothiazine-3-carboxamide, 1,1-dioxide;

4-hydroxy-2-methyl-N-[5-[(nonylsulfinyl)methyl]-3-isoxazolyl]-2H-1,2-benzothiazine-3-carboxamide, 1,1-dioxide;

N-[5-[[[(3,4-dichlorophenyl)methyl]thio]methyl-3-isoxazolyl]-4-hydroxy-2-methyl-2H-1,2-benzothiazine-3-carboxamide, 1,1-dioxide;

N-[5-[[[(3,4-dichlorophenyl)methyl]sulfonyl]methyl]-3-isoxazolyl]-4-hydroxy-2-methyl-2H-1,2-benzothiazine-3-carboxamide, 1,1-dioxide;

N-[5-[[[(3,4-dichlorophenyl)methyl]sulfinyl]methyl]-3-isoxazolyl]-4-hydroxy-2-methyl-2H-1,2-benzothiazine-3-carboxamide, 1,1-dioxide;

N-[5-[[[(3,4-dimethoxyphenyl)methyl]thio]methyl-3-isoxazolyl]-4-hydroxy-2-methyl-2H-1,2-benzothiazine-3-carboxamide, 1,1-dioxide;

N-[5-[[[(3,4-dimethoxyphenyl)methyl]sulfonyl]methyl]-3-isoxazolyl]-4-hydroxy-2-methyl-2H-1,2-benzothiazine-3-carboxamide, 1,1-dioxide; and N-[5-[[[3,4-dihydroxyphenyl)methyl]thio]methyl]-3-isoxazolyl]-4-hydroxy-2-methyl-2H-1,2-benzothiazine-3-carboxamide, 1,1-dioxide.

The compounds of this invention are useful as antiinflammatory agents, antipyretics, and analgesics in several mammalian species. When administered orally in rats at a dose of 20–200 mg/kg, they are able to cause reduction in swelling of the paw induced by injection into the foot pads of an irritant such as carrageenin. Therapeutically or prophylactically administered orally or intraperitoneally at a dose of 15–200 mg/kg, the compounds inhibit adjuvant induced polyarthritis in the rat. Intraperitoneal or oral doses of 25–100 mg/kg are sufficient to inhibit yeast induced hyperthermia in the rat. At intraperitoneal or oral doses of 25–200 mg/kg they exhibit a significant analgesic effect as determined by the phenylquinone writhing procedure in mice.

Generally speaking, these compounds are indicated in conditions such as pain resulting from arthritis, bursitis, and the like. A daily dosage regimen of about 0.5 grams to about 2 grams in several divided doses is recommended for a mammal weighing about 70 kg body weight to relieve the pain and swelling associated with these conditions. These compounds are administered either orally or by injection.

In order to use these compounds, they are formulated into dosage forms such as tablets or syrups by blending with an inert pharmaceutical carrier such as lactose or simple syrup by methods well known to the pharmacist's art. For injectable dosage forms, they are formulated with vehicles such as water, peanut oil, sesame oil, and the like. In these dosage forms, the active ingredient is from about 0.5 grams to 1 gram per dosage unit.

Accordingly, the present invention includes a pharmaceutical composition for treating pain resulting from inflammation such as arthritis or bursitis comprising an effective amount of a compound of formula 1 in admixture with an inert pharmaceutical carrier.

The present invention also provides for a method of treating mammals suffering from pain resulting from inflammation such as, arthritis or bursitis, comprising administering to said mammal an effective amount of a compound of the formula 1 in the form of a pharmaceutical composition.

According to the present invention, the above compounds are prepared by a reaction scheme as follows:

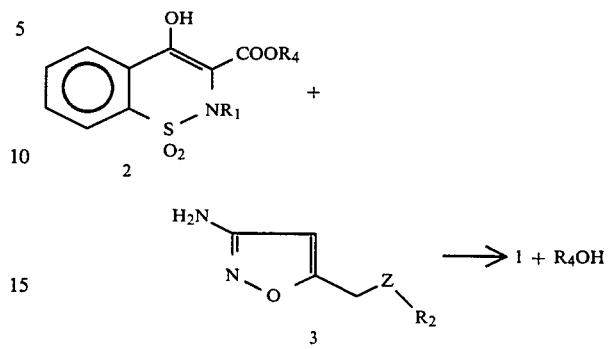

wherein $R_1$, $R_2$, and Z are defined above and $R_4$ is alkyl of 1 to 4 carbon atoms.

Generally speaking, starting compound 2 is refluxed with 3-amino-5-(substituted hetero)methyl isoxazole (3) in an inert solvent such as xylene. In a preferred embodiment of the present invention, the reactants are refluxed in the presence of a molecular sieve which promote the desired reaction by removing the alcohol which is formed as a by-product. The use of molecular sieve results in a more convenient and practical process in that lengthy distillation to remove the alcohol is no longer required. Typically the reaction is carried out in a Soxhlet apparatus with the molecular sieves contained in the thimble.

Examples of the molecular sieves, which can be used in this process, are commercially available molecular sieves under the trade name Linde type 4A molecular sieve from Matheson Coleman & Bell Company.

The compounds of the formula 1 are capable of existing in tautomeric forms which is illustrated by the following equilibrium. Both forms are included by the present invention.

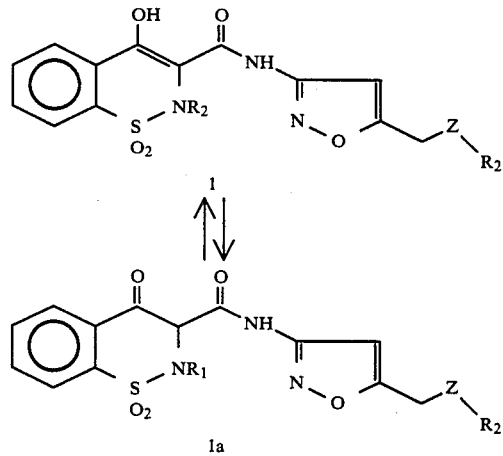

The starting materials of formula 2 are known compounds and are prepared in accordance with the description in U.S. Pat. Nos. 3,960,856 and 3,501,466.

Starting compounds 3-amino-5-(substituted-heteromethyl)-isoxazoles are prepared as shown by the following flow diagram:

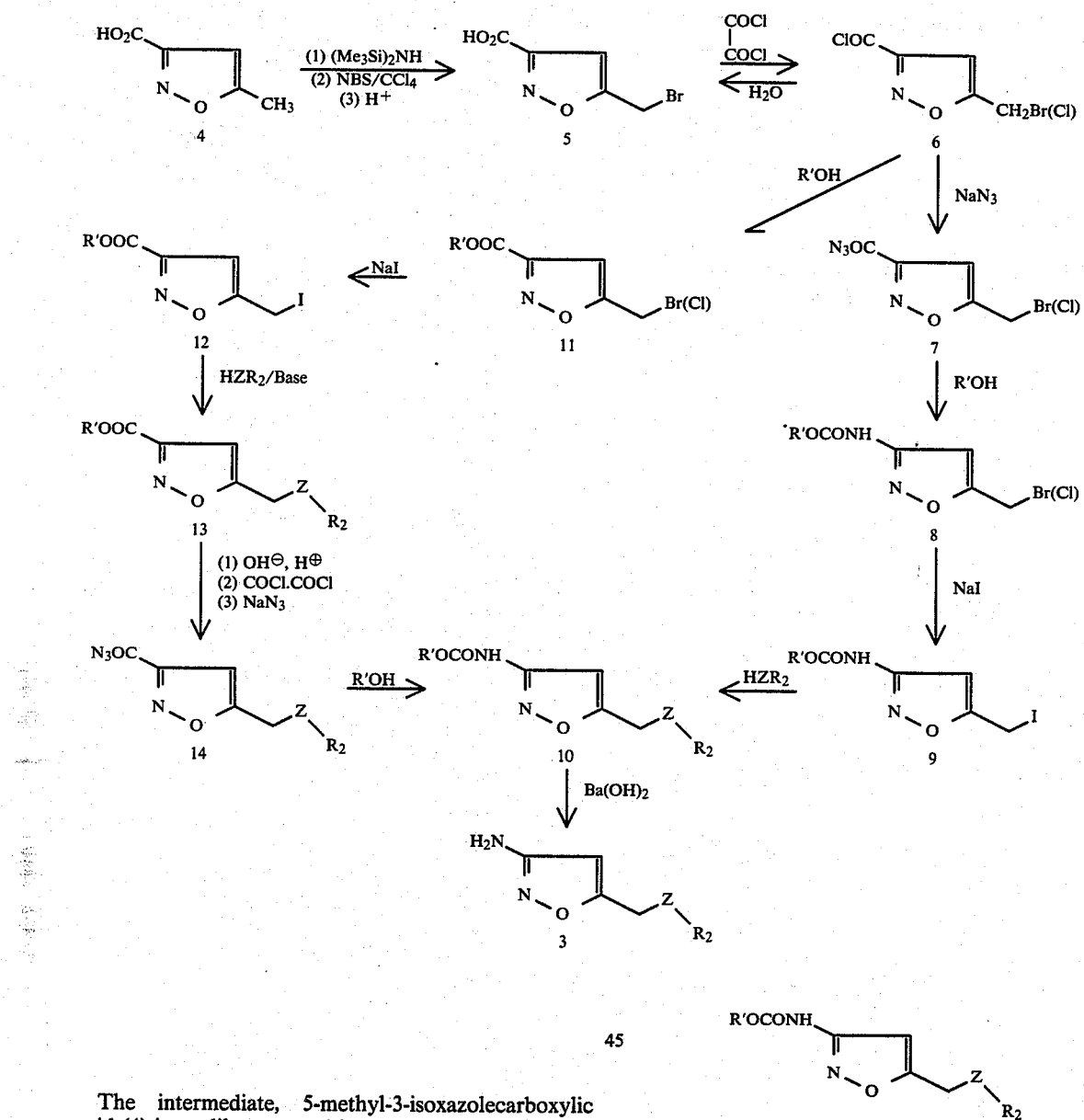

The intermediate, 5-methyl-3-isoxazolecarboxylic acid (4) is readily prepared in accordance with the description set forth in the U.S. Pat. No. 2,908,688 issued Oct. 13, 1959.

Accordingly the present invention encompasses the novel intermediates illustrated in the above flow diagram as well as the process for preparing the intermediate of formula 3.

Preferred intermediates are compounds of the formula

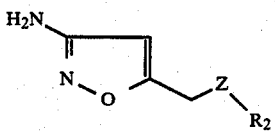

wherein Z and $R_2$ are as defined for the compounds of formula 1.

Also preferred intermediates are compounds of the formula

R'OCONH
$$\underset{N\diagdown_O}{\diagup\!\!\!\diagdown}\diagdown Z\diagdown R_2$$
10 wherein Z and $R_2$ are as defined for the compounds of formula 1 and R' is akyl of 1 to 6 carbon atoms, for example, methyl.

Compounds of formula 1 in accordance with the present invention where Z is sulfinyl (i.e. S=O) are prepared by oxidation of the corresponding thio-compound (i.e. where Z is sulfur) with one equivalent of hydrogen peroxide. Correspondingly, the sulfonyl compounds (where Z is $SO_2$) are prepared by oxidation of the thio-compounds with two equivalents of hydrogen peroxide.

Compounds of formula 1 where $R_2$ is dihydroxyphenyl are conveniently prepared by reaction of boron tribromide on the corresponding dimethoxyphenyl compounds.

Thus the present invention further includes a process for the preparation of a compound of the formula 3 which comprises treating a compound of formula 10, as defined above, with an alkaline earth metal hydroxide, for example, calcium, strontium, and especially barium hydroxide, at the reflux temperature of the solvent such as an alcohol, e.g., ethanol.

The corresponding salts with metals or with amines are prepared by treating the above compounds of formula 1 with the desired base, e.g., sodium alkoxide, potassium alkoxide, sodium hydroxide, potassium hydroxide, calcium hydroxide, aluminum hydroxide, pyrrolidine, arginine, N-methylD-glucamine, and the like by conventional procedures.

The terms alkyl, alkoxy, alkylthio, and alkanoyl used above have been designated by certain number of carbon atoms and include whenever applicable straight and branched chain hydrocarbons as n-propyl, isopropyl, n-butyl, sec-butyl, iso-butyl, t-butyl, and the like.

The following examples are illustrative of the invention. All temperatures are in degree centigrade and melting points are not corrected.

EXAMPLE 1

4-Hydroxy-N-[5-(methoxymethyl)-3-isoxazolyl]-2-methyl-2H-1,2-benzothiazine-3-carboxamide 1,1-dioxide A mixture of 0.52 g (4 mmole) of 5-(methoxymethyl)-3-isoxazolamine, 1.08 g (4 mmole) of methyl 4-hydroxy-2-methyl-2H-1,2-benzothiazine-3-carboxylate 1,1-dioxide, and 100 ml of xylene is heated at reflux for six hours in a soxhlet apparatus, the thimble of which contains 20 g of Linde type 4A molecular sieve. The reaction mixture is filtered to clarify it and is allowed to stand at room temperature overnight when the product crystallizes out. The product is filtered, washed with methanol-ether mixture, and then recrystallized from methanol to give 0.326 g of white crystals, mp 218°-223° C. dec.

EXAMPLE 2

The procedure described in Example 1 is repeated to prepare the following 4-hydroxy-2-methyl-2H-1,2-benzothiazine-3-carboxamides 1,1-dioxides, starting from methyl 4-hydroxy-2-methyl-2H-1,2 benzothiazine-3-carboxylate 1,1-dioxide and the appropriate 5-substituted heteromethyl-3-isoxazolamines in each case:

4-Hydroxy-N-[5-[(benzyloxy)methyl]-3-isoxazolyl]-2-methyl-2H-1,2-benzothiazine-3-carboxamide, 1,1-dioxide, mp 206°-207.5° C.;

4-Hydroxy-N-[5-[(butylthio)methyl]-3-isoxazolyl]-2-methyl-2H-1,2-benzothiazine-3-carboxamide 1,1-dioxide, mp 155°-156° C.;

4-Hydroxy-N-[5-[(octyloxy)methyl]-3-isoxazolyl]-2-methyl-2H-1,2-benzothiazine-3-carboxamide 1,1-dioxide, mp 152°-154° C.;

4-hydroxy-N-[5-(octylthio)methyl]-3-isoxazolyl-2-methyl-2H-1,2-benzothiazine-3-carboxamide, 1,1-dioxide, mp 135°-136° C.;

N-[5-[(heptylthio)methyl]-3-isoxazolyl]-4-hydroxy-2-methyl-2H-1,2-benzothiazine-3-carboxamide, 1,1-dioxide, mp 132°-133° C.;

N-[5-[(decylthio)methyl]-3-isoxazolyl]-4-hydroxy-2-methyl-2H-1,2-benzothiazine-3-carboxamide, 1,1-dioxide, mp 1275°-128.5° C.;

4-hydroxy-2-methyl-N-[5-[(nonylthio)methyl]-3-isoxazolyl]-2H-1,2-benzothiazine-3-carboxamide, 1,1-dioxide, mp 129°-130° C.;

N-[5-[[[(3,4-dichlorophenyl)methyl]thio]methyl-3-isoxazolyl]-4-hydroxy-2-methyl-2H-1,2-benzothiazine-3-carboxamide, 1,1-dioxide, mp 188°-189° C.;

N-[5-[[[(3,4-dimethoxyphenyl)methyl]thio]methyl]-3-isoxazolyl]-4-hydroxy-2-methyl-2H-1,2-benzothiazine-3-carboxamide, 1,1-dioxide, mp 164°-167° C.; and 4-hydroxy-2-methyl-N-[5-[[[5-[(octyloxy)methyl]-3-isoxazolyl]amino]methyl]-3-isoxazolyl]-2H-1,2-benzothiazine-3-carboxamide, 1,1-dioxide;

EXAMPLE 2a

N-[5-[(decylsulfonyl)methyl]-3-isoxazolyl]-4-hydroxy-2-methyl-2H-1,2-benzothiazine-3-carboxamide, 1,1-dioxide 1.02 g (0.002 mole) of N-[5-[(decylthio)methyl]-3-isoxazolyl]-4-hydroxy-2-methyl-2H-1,2-benzothiazine-3-carboxamide, 1,1-dioxide is suspended in 25 ml of acetic acid and 2.23 g (0.02 mole) of 30.5% hydrogen peroxide in 5 ml of acetic acid is added. The mixture is warmed on a steam bath for 30 minutes to obtain a solution. The solution is evaporated to dryness and the pinkish-white solid residue is recrystallized from acetic acid-water mixture (10:3 v/v) to yield white crystals of the the title compound (650 mg), mp 150.5°-153° C.

EXAMPLE 2b

The procedure detailed in Example 2a is repeated to prepare the following 4-hydroxy-2-methyl-2H-1,2-benzothiazine-3-carboxamide, 1,1-dioxides, starting from the appropriate N-[5-[(alkyl or aralkylthio)-methyl]-3-isoxazolyl]-4-hydroxy-2-methyl-2H-1,2-benzothiazine-3-carboxamide, 1,1-dioxides;

N-[5-[(butylsulfonyl)methyl]-3-isoxazolyl]-4-hydroxy-2-methyl-2H-1,2-benzothiazine-3-carboxamide, 1,1-dioxide, mp 196°-199° C.

4-hydroxy-2-methyl-N-[5-(octylsulfonyl)methyl]-3-isoxazolyl[-2H-1,2-benzothiazine-3-carboxamide, 1,1-dioxide, mp 145°-148° C.

N-[5-[(heptylsulfonyl)methyl]-3-isoxazolyl]-4-hydroxy-2-methyl-2H-1,2-benzothiazine-3-carboxamide, 1,1-dioxide, mp 141°-147° C.

4-hydroxy-2-methyl-N-[5-[(nonylsulfonyl)methyl]-3-isoxazolyl]-2H-1,2-benzothiazine-3-carboxamide, 1,1-dioxide, mp 150°-151° C.

N-[5-[[[(3,4-dichlorophenyl)methyl]sulfonyl]methyl]-3-isoxazolyl]-4-hydroxy-2-methyl-2H-1,2-benzothiazine-3-carboxamide, 1,1-dioxide, mp 203°-205° C. (dec.); and N-[5-[[[(3,4-dimethoxyphenyl)methyl]sulfonyl]methyl]-3-isoxazolyl]-4-hydroxy-2-methyl-2H-1,2-benzothiazine-3-carboxamide, 1,1-dioxide, mp 215°-217° C.

EXAMPLE 2c

N-[5-[nonylsulfinyl)methyl]-3-isoxazolyl]-4-hydroxy-2-methyl]-2H-1,2-benzothiazine-3-carboxamide, 1,1-dioxide 0.987 g (2 mmol) of N-[5-[(nonylthio)methyl]-3-isoxazolyl]-4-hydroxy-2-methyl-2H-1,2-benzothiazinecarboxamide, 1,1-dioxide is dissolved in 50 ml of acetic acid and 0.223 g (2 mmol) of 30.5% hydrogen peroxide, dissolved in 5 ml of acetic acid, is added to the solution. The reaction mixture is allowed to stand at room temperature for 18 hours and is then evaporated to dryness on a rotary evaporator. The solid residue is recrystallized from diethyl ether to yield off-white crystals of the title compound, (0.65 g), mp 127°-129° C.

EXAMPLE 2d

The procedure detailed in Example 2c is repeated to prepare the following 4-hydroxy-2-methyl-2H-1,2-benzothiazine-3-carboxamide, 1,1-dioxides, starting from the appropriate N-[5-[(alkyl or aralkylthio)-methyl]-3-isoxazolyl]-4-hydroxy-2-methyl-2H-1,2-benzothiazine-3-carboxamide, 1,1-dioxides:

N-[5-[(heptylsulfinyl)methyl]-3-isoxazolyl]-4-hydroxy-2-methyl-2H-1,2-benzothiazine-3-carboxamide, 1,1-dioxide, mp 134°–136° C.

4-hydroxy-2-methyl-N-[5-[(octylsulfinyl)methyl]-3-isoxazolyl]-2H-1,2-benzothiazine-3-carboxamide, 1,1-dioxide, mp 130°–132° C.

N-[5-[(decylsulfinyl)methyl]-3-isoxazolyl]-4-hydroxy-2-methyl-2H-1,2-benzothiazine-3-carboxamide, 1,1-dioxide, mp 121°–123° C.

N-[5-[(butylsulfinyl)methyl]-3-isoxazolyl]-4-hydroxy-2-methyl-2H-1,2-benzothiazine-3-carboxamide, 1,1-dioxide, mp 186°–188° C.

N-[5-[[[(3,4-dichlorophenyl)methyl]sulfinyl]methyl]-3-isoxazolyl]-4-hydroxy-2-methyl-2H-1,2-benzothiazine-3-carboxamide, 1,1-dioxide, mp 196°–200° C.

EXAMPLE 2e

4-Hydroxy-N-[5-[[[(3,4-dihydroxyphenyl)methyl]thiol]-methyl-3-isoxazolyl]-2-methyl-2H-1,2-benzothiazine-3-carboxamide, 1,1-dioxide A solution of boron tribromide (1M, 10 ml) in methylene chloride is added to a cold (−70° C.) solution of 4-hydroxy-N-[5-[[[3,4-dimethoxyphenyl)methyl]thiol]-methyl-3-isoxazolyl]-2-methyl-2H-1,2-benzothiazine-3-carboxamide, 1,1-dioxide (0.518 g; 1 m mol) over 5 minutes. The amber solution is kept cold for 30 minutes, then allowed to rise to room temperature and let stand for 16 hours. The solution is chilled, decomposed with 25 ml of cold water and 25 ml of methanol and evaporated to dryness. The residue is redissolved in methanol and evaporated to dryness. The process is repeated several times to give a tan residue that is washed with water, and recrystallized from isopropanol to give light tan solid (0.32 g), mp 210°–213° C. (dec.).

EXAMPLE 3

5-(Bromomethyl)-3-isoxazolecarbonyl chloride and 5-(chloromethyl)-3-isoxazolecarbonyl chloride 36.8 g (0.29 mole) of 5-methyl-3-isoxazolecarboxylic acid is suspended in 250 ml of carbon tetrachloride and then treated with 27.5 g (0.17 mole) of hexamethyldisilazine. The mixture is heated to reflux for one hour and the resulting yellow solution is evaporated to dryness to give an oil. The trimethylsilyl ester is dissolved in 300 ml of fresh carbon tetrachloride and is treated with 89 g (0.5 mole) of N-bromosuccinimide and 2.0 g of benzoyl peroxide. The reaction mixture is heated and illuminated by a Cole-Parmer Dynalume high intensity lamp, so that moderate reflux is maintained. After one hour of reaction, the mixture is charged with an additional 10 g (0.056 mole) of N-bromosuccinimide and 0.5 g of benzoyl peroxide, and maintained under reflux for an additional 0.5 hour. The reaction mixture is cooled and the succinimide is filtered off. The red filtrate is evaporated to dryness and the residue is taken up in THF containing 5 ml of 4N HCl. The solution is heated on a steam bath for five minutes and then evaporated to a red oily solid which when triturated with ether gives 30.6 g of crude bromo-acid. The crude acid is dried under vacuum at room temperature for 15 hours over $P_2O_5$.

The crude 5-(bromomethyl)-3-isoxazole-carboxylic acid (18 g) is dissolved in 150 ml of dry THF and 36.38 g (0.28 mole) of oxalyl chloride is added. The reaction mixture is heated to reflux for two hours. The solvent and excess oxalyl chloride is removed under reduced pressure and the brown liquid is distilled. The fraction (6.27 g) boiling at 60°–62° C./0.1 mm is collected and used without further purification. NMR and analysis indicates that it is a mixture of 5-chloromethyl and 5-(bromomethyl)-3-isoxazolecarbonyl chloride.

EXAMPLE 4

5-Bromomethyl-3-isoxazolecarboxylic acid

The distilled 5-(bromomethyl)-3-isoxazolecarbonyl chloride (1 g) is dissolved in 2 ml of acetone, cooled to 0° C. and 3 ml of water is added to the solution. The solution is allowed to stand at room temperature for one hour and then the solvent is removed under reduced pressure giving 0.9 g of the acid. It is dried over $P_2O_5$ for three days and has mp 143°–148° C.

EXAMPLE 5

5-(Bromomethyl)-3-isoxazolecarbonyl azide and 5-(chloromethyl)-3-isoxazolecarbonyl azide A solution of 2.24 g (0.01 mole) of distilled acid chloride for Example 3 in 5 ml of acetone is cooled in ice-water and a solution of 0.68 g (0.0105 mole) of sodium azide in 2 ml of water is added rapidly and allowed to stand for 15 minutes. The solution is evaporated to dryness and the white solid residue is washed with cold water and dried under vacuum overnight over $P_2O_5$. The acid azide (1.82 g) is recrystallized from absolute ethanol as white needles, mp 75°–76.5° C.

EXAMPLE 6

5-(Bromomethyl)-3-[(methoxycarbonyl)amino]isoxazole and 5-(chloromethyl)-3-[(methoxycarbonyl)amino]isoxazole A solution of 1.16 g (~5.0 mmole) of a mixture of 5-(bromomethyl)-3-isoxazolecarbonyl azide and 5-(chloromethyl)-3-isoxazolecarbonyl azide of Example 5 in 10 ml of methanol and 25 ml of p-dioxane is heated to reflux in an atmosphere of nitrogen for six hours, and allowed to stand overnight at room temperature. The reaction mixture is evaporated to dryness to give 1.23 g of off-white solid which is recrystallized from isopropyl ether, mp 140°–143° C.

EXAMPLE 7

5-(Iodomethyl)-3-[(methoxycarbonyl)amino]isoxazole

A solution of 6 g (0.04 mole) of sodium iodide in 50 ml of acetone is added to a solution of 6.5 g (~0.027 mole) of a mixture of 5-(bromomethyl) and 5-(chloromethyl)-3-[(methoxycarbonyl)amino]isoxazole in 25 ml of acetone. The reaction mixture is heated to reflux for two hours and then allowed to stand at room temperature overnight. The inorganic salts are filtered off and the filtrate is evaporated to dryness. The residue is washed thoroughly with water and dried to give 7.2 g of yellowish tan solid. The crude product is recrystallized from methanol to give 3.3 g of white crystals, mp 154°–156° C. dec.

EXAMPLE 8

5-[(Benzyloxy)methyl]-3-isoxazolamine

A 700 mg amount of 60% sodium hydride in mineral oil (0.42 g NaH=0.0175 mole) is washed with dry hexane, suspended in 5 ml of THF and then treated with 20 ml of benzyl alcohol. After the evolution of $H_2$ has ceased, the pale-yellow solution is warmed up to 70°, and then treated with 3.5 g (0.0125 mole) of 5-Iodomethyl-3-methoxycarbonyl aminoisoxazole in 60 ml of benzyl alcohol. The reaction mixture is warmed at 74° C. for one hour and then allowed to stand at room temperature overnight. The reaction mixture is acidified with 7 ml of 1N HCl, and the excess benzyl alcohol is distilled off. The crude 5-[(benzyloxy)-methyl]-3-isoxazolamine (4.3 g) is isolated in the usual way. The crude material is mixed with 40 ml of ethanol, 40 ml of water, and 2.74 g (0.016 mole) of barium hydroxide and refluxed under nitrogen for 1.5 hours. The reaction mixture is cooled, treated with dry ice, and the barium carbonate is filtered off. The filtrate is evaporated to dryness and the product (0.64 g) is isolated by preparative layer chromatography, mp 51°–53° C.

EXAMPLE 9

The procedure described in Example 8 is repeated to prepare the following 5-[(substituted hetero)methyl]-3-isoxazoleamines:

5-methoxymethyl-3-isoxazolamine, mp 49°–52° C.;
5-[(butylthio)methyl]-3-isoxazolamine, oil;
5-[(octyloxy)methyl]-3-isoxazolamine, mp 50°–52° C.;
5-[(Heptylthio)methyl]-3-isoxazolamine, mp 47°–50° C.;
5-[(Octylthio)methyl]-3-izoxazolamine, mp 53.5°–55° C.;
5-[(Nonylthio)methyl]-3-isoxazolamine, mp 63°–66° C.;
5-[(Decylthio)methyl]-3-isoxazolamine, mp 63°–66° C.;
5-[[[(3,4-Dichlorophenyl)methyl]thio]methyl]-3-isoxazolamine, mp 89°–91° C.; and
5-[[[(3,4-Dimethoxyphenyl)methyl]thio]methyl]-3-isoxazolamine, mp 83.5°–85.5° C.

EXAMPLE 10

Methyl 5-(Bromomethyl)-3-isoxazolecarboxylate and methyl 5-(chloromethyl)-3-isoxazolecarboxylate A solution of 49 g (~0.22 mole) of crude 5-bromo(chloro)methylisoxazole-3-carboxylic acid chloride from Example 3 in 100 ml of ether is added to 25 ml of methanol in an ice bath under $N_2$. The reaction mixture is allowed to reach room temperature and then evaporated to dryness. The crude ester is dissolved in ether, treated with anhydrous potassium carbonate. The solvent is removed under reduced pressure and the product is recrystallized from ethercyclohexane to give 24.4 g of off-white platelets, mp 60°–66° C.

EXAMPLE 11

Methyl 5-(iodomethyl)-3-isoxazolecarboxylate

A solution of 0.45 g (3 mmole) of sodium iodide in 5 ml of acetone is mixed with a solution of 0.5 g (2.4 mmole) of methyl 5-bromo(chloro)methyl 3-isoxazolecarboxylate. The mixture is warmed on a steam bath for 30 minutes and the inorganic material filtered off. The filtrate is evaporated to dryness and the residue is washed with water and dried over $P_2O_5$ giving 0.58 g of the desired product, mp 91°–95° C.

EXAMPLE 12

Methyl 5-(methoxymethyl)-3-isoxazolecarboxylate

A solution of 1.34 g (5 mmole) of methyl 5-(iodomethyl)-3-isoxazolecarboxylate in 20 ml of methanol and 5 ml of THF is added to a solution of methanol and 5 ml of THF is added to a solution of sodium methoxide prepared from 0.15 g (6.5 mmole) sodium and 10 ml of methanol. The reaction mixture is stirred at room temperature for four hours, heated to reflux for 30 minutes, and then worked up as usual giving 0.65 g of product. The crude ester is recrystallized from ether-cyclohexane mixture to give 0.33 g of off-white solid, mp 47.5°–49° C.

EXAMPLE 13

5-(Methoxymethyl)-3-isoxazolecarbonyl azide

A 6.0 g (0.035 mole) amount of methyl 5-(methoxymethyl)-3-isoxazolecarboxylate is hydrolyzed with 50 ml 1N sodium hydroxide solution at 40° for five minutes and then acidified with 4N HCl and extracted with chloroform as usual. The crude dry acid (4.0 g) is converted to the acid chloride by treatment with oxalyl chloride (7 ml) in THF (10 ml) at reflux temperature for four hours. The solvent is removed and the crude acid chloride is reacted with sodium azide as described in Example 5, giving 4.65 g of solid. The crude acid azide is recrystallized from ether-n-hexane to give 2.8 g of off-white solid, mp 55°–58° C. dec.

EXAMPLE 14

5-(Methoxymethyl)-3-[(methoxycarbonyl)amino]isoxazole

A mixture of 2.5 g (0.0137 mole) of 5-(methoxy methyl)-3-isoxazolecarbonyl azide, 15 ml of methanol and 25 ml of p-dioxane is heated to reflux for 16 hours. The solvent is removed under reduced pressure and the solid residue is triturated with ether-cyclohexane giving an off-white solid, mp 90°–91° C.

EXAMPLE 15

5-(Methoxymethyl)-3-isoxazolamine

A mixture of 1.86 g (0.01 mole) of 5-(methoxymethyl)-3-[(methoxycarbonyl)amino]isoxazole and 2.06 g (0.012 mole) of $Ba(OH)_2$ in 20 ml of ethanol and 20 ml of water is heated to reflux for one hour. Dry ice is added lowering the pH to 5 and the resulting emulsion is evaporated to dryness. The residue is extracted with boiling ether and the ether extract is evaporated to dryness giving 1.1 g of colorless liquid which crystallizes on standing. The amine is recrystallized from ether-n-pentane as white crystals, mp 49°–52° C.

We claim:

1. A compound being 5-[(heptylthio)methyl]-3-isoxazolamine.
2. A compound being 5-[(octylthio)methyl]-3-isoxazolamine.
3. A compound being 5-[(nonylthio)methyl]-3-isoxazolamine.
4. A compound and being 5-[(decylthio)methyl]-3-isoxazolamine.
5. A compound and being 5-[[[(3,4-dichlorophenyl)methyl]thio]methyl]-3-isoxazolamine.
6. A compound and being 5-[[[(3,4-dimethoxyphenyl)methyl]thio]methyl]-3-isoxazolamine.

* * * * *